United States Patent
Baker

(10) Patent No.: US 8,414,595 B2
(45) Date of Patent: Apr. 9, 2013

(54) ORTHOPEDIC CAST REMOVER

(75) Inventor: Russell Baker, Sunnyside, NY (US)

(73) Assignees: David Feldman, New York, NY (US);
Beth Feldman, Englewood, NJ (US);
David Berk, East Brunswick, NJ (US)

(*) Notice: Subject to any disclaimer, the term of this patent is extended or adjusted under 35 U.S.C. 154(b) by 0 days.

(21) Appl. No.: 13/126,469

(22) PCT Filed: Nov. 2, 2009

(86) PCT No.: PCT/US2009/062954
§ 371 (c)(1),
(2), (4) Date: Jul. 22, 2011

(87) PCT Pub. No.: WO2010/051529
PCT Pub. Date: May 6, 2010

(65) Prior Publication Data
US 2011/0270263 A1    Nov. 3, 2011

Related U.S. Application Data

(60) Provisional application No. 61/110,012, filed on Oct. 31, 2008.

(51) Int. Cl.
*A61F 5/04* (2006.01)

(52) U.S. Cl.
USPC ........................................ 606/105.5

(58) Field of Classification Search ............... 606/86 R, 606/105, 105.5
See application file for complete search history.

(56) References Cited

U.S. PATENT DOCUMENTS

| 2,344,262 | A | * | 3/1944 | Odierna et al. | 30/370 |
| 3,534,474 | A | | 10/1970 | Smith | |
| 5,020,226 | A | * | 6/1991 | Chabbert | 30/390 |
| 5,056,203 | A | * | 10/1991 | Miller | 407/29.14 |
| 5,309,962 | A | * | 5/1994 | McCord et al. | 144/237 |
| 5,674,119 | A | * | 10/1997 | DesRosiers | 451/344 |
| 5,895,361 | A | * | 4/1999 | Turturro | 600/562 |

(Continued)

FOREIGN PATENT DOCUMENTS

| EP | 0752240 | 1/1997 |
| KR | 1020050105560 | 11/2005 |

(Continued)

OTHER PUBLICATIONS

Great Britain Search Report dated Apr. 30, 2012 from corresponding GB Application No. 1107374.9.

(Continued)

*Primary Examiner* — Anu Ramana
(74) *Attorney, Agent, or Firm* — Katten Muchin Rosenman LLP

(57) ABSTRACT

Systems, apparatuses and methods are disclosed for an orthopedic cast remover. The cast remover includes a rotatable cutting assembly having first and second cutting wheel sandwiched between a smaller-sized hub, where the space between the first and second wheel defines a passage in which fractured material may pass. A shear is coupled to the cutting assembly and is positioned in the passage, where edges of the shear are configured to engage with each of the cutting wheels. During operation, rigid material, such as a cast shell, passes along a top surface of the shear and is fractured into a predetermined width at a point where the shear edges engage with the rotating cutting wheels. The fractured material is fed into the passage for easy removal.

11 Claims, 14 Drawing Sheets

U.S. PATENT DOCUMENTS

| | | | |
|---|---|---|---|
| 6,558,394 B2 * | 5/2003 | Lee | 606/105.5 |
| 6,976,992 B2 * | 12/2005 | Sachatello et al. | 606/205 |
| 2002/0038124 A1 | 3/2002 | Lee | |
| 2003/0065334 A1 | 4/2003 | Hobgood et al. | |

FOREIGN PATENT DOCUMENTS

| | | |
|---|---|---|
| KR | 100686710 | 2/2007 |
| WO | 2005092267 | 10/2005 |
| WO | 2005110294 | 11/2005 |

OTHER PUBLICATIONS

International Search Report dated Jun. 14, 2010 from the corresponding PCT/US2009/062954.

International Preliminary Report on Patentability dated May 3, 2011 from the corresponding PCT/US2009/062954.

* cited by examiner

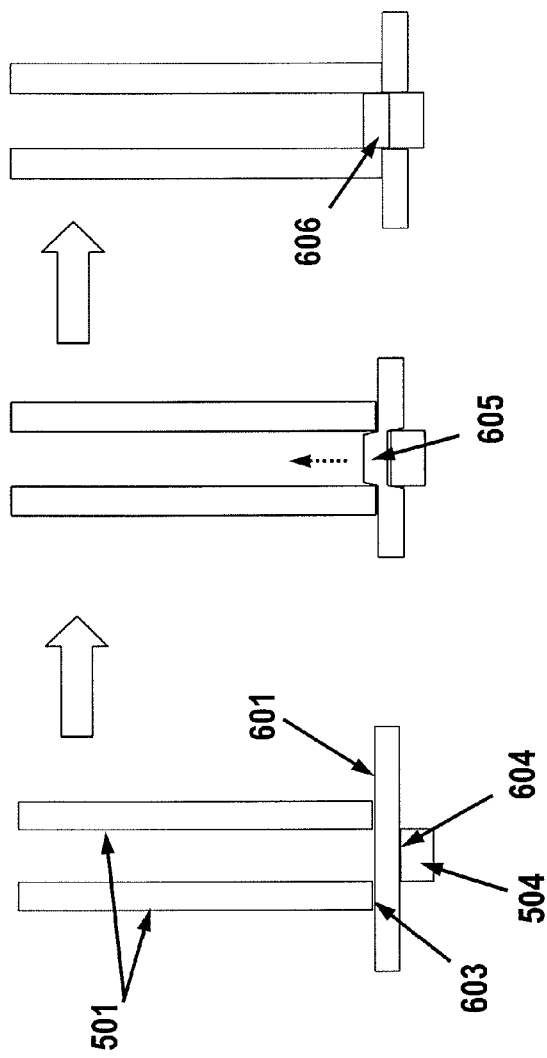

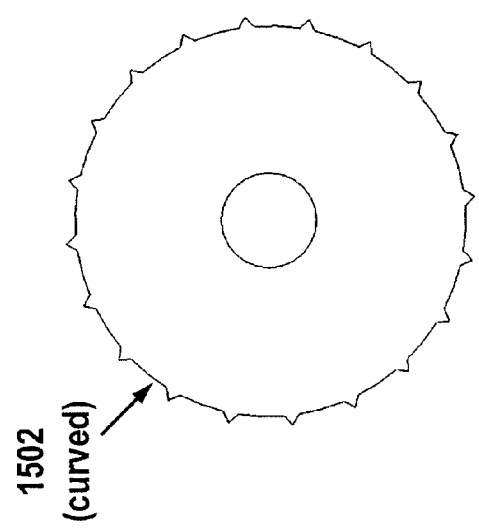
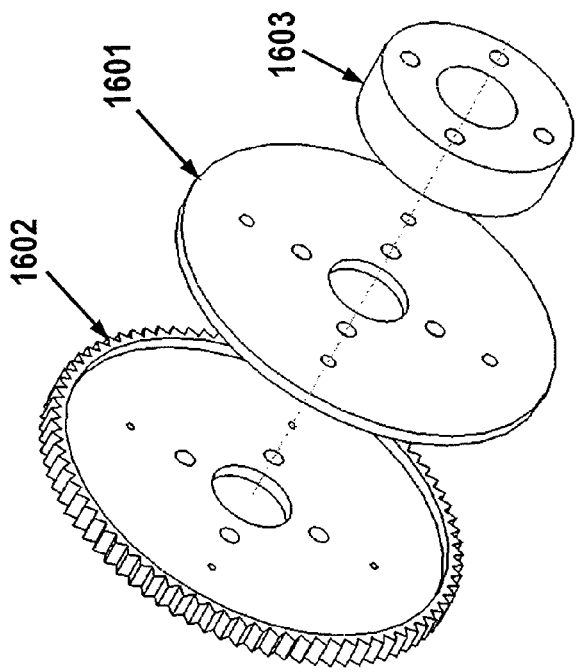

ORTHOPEDIC CAST REMOVER

RELATED APPLICATIONS

The present application claims priority to provisional application 61/110,012, titled "Orthopedic Saw", filed Oct. 31, 2008, which is incorporated by reference in its entirety herein.

TECHNICAL FIELD

The present disclosure relates to systems, apparatuses and methods relating to medical cutting devices. More specifically, the disclosure relates, but is not limited to, cast removal systems that are designed for the removal of orthopedic casts generally applied for immobilization. Immobilization is considered essential for the proper healing of broken bones and other internal trauma.

BACKGROUND INFORMATION

Orthopedic casts typically consist of three layers. The outer layer, or the "shell", is typically constructed of a quick drying bandage that hardens and becomes rigid upon drying. The shell layer provides the necessary rigidity and is typically made of either plaster, for its high formability, or fiberglass, for its faster drying time and lighter construction. The middle layer typically consists of padding to separate the rigid shell from the skin and provide comfort. The inner layer is typically a cotton gauze that interfaces directly with the skin and is also for comfort.

Most casts are removed using an electrically powered, oscillating saw. The blade of the saw is typically configured as a circular blade with fine teeth, where the blade oscillates about the center of the saw. Examples of such saws include the Stryker® 940 cast cutter, American Orthopaedic™ BSN 0295-200 cast cutter, and De Soutter CleanCast™ oscillating cast saw.

Several aspects of such a conventional design result in less than optimal performance. The saw can not make continuous cuts, but is applied successively in a line. Due to the circular geometry of the blade, the depth of the cut varies. As a result, portions of the cut away from the center of the blade application are often not fully separated and must be re-cut with the saw. Additionally, due to the high velocity of the blade, a saw is typically used to cut only through the shell layer, where scissors or other implements are used to cut through the padding and gauze. The high frequency oscillations produce uncomfortable noise levels and considerable dust when cutting. Moreover, the use of an oscillating saw for cast removal creates a potential for iatrogenic injury and patient discomfort. Burns and abrasions can occur from the heat created by frictional forces and direct blade contact.

SUMMARY

The present disclosure describes systems apparatuses and methods for making cast removal safer and easier. Under exemplary embodiments described below, a specially-configured saw should be able to cut through all layers of the cast in one pass while also minimizing the potential for patient skin coming into contact with the cutting surfaces. Additionally, the embodiments operate using a lower level of oscillation/velocity, resulting in reduced noise, heat buildup, as well as dust and debris production. Under normal operation, the disclosed saw replaces high velocity material removal methodologies of conventional designs with ones based on slow, high-force shearing.

BRIEF DESCRIPTION OF THE DRAWINGS

FIGS. 6A-6C illustrates an exemplary fracturing process on a cast-like structure;

FIG. 7 illustrates a rendering of a cast-like structure during the fracturing process shown in FIGS. 6A-6B, above;

FIGS. 15A-15B illustrates alternate embodiments of cutting wheels for a cutting wheel assembly;

FIG. 16 illustrates a cutting wheel assembly under another exemplary embodiment that further includes an internal blade

DETAILED DESCRIPTION

Figure 1:
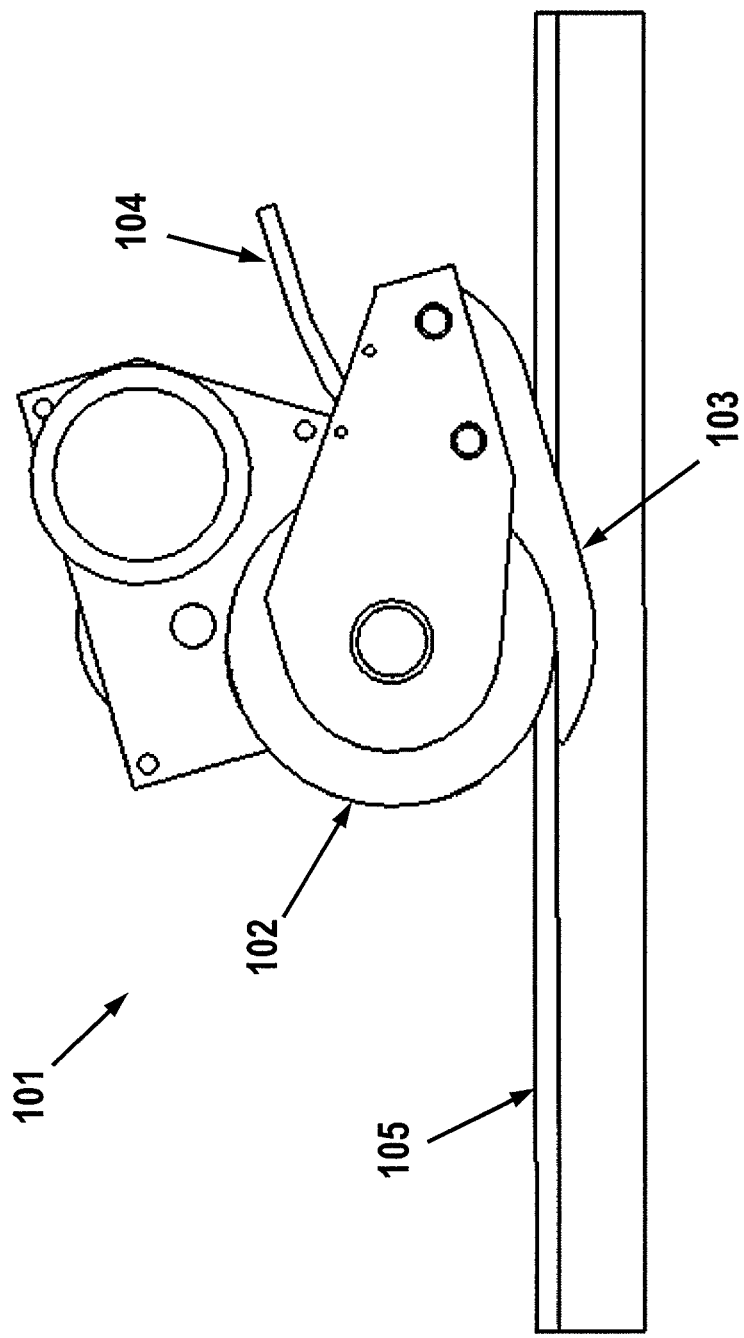
FIG. 1 illustrates a side view of an orthopedic cast remover under an exemplary embodiment.

In the following detailed description of the invention, reference is made to the accompanying drawings which form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, electrical, and mechanical changes may be made without departing from the scope of the present invention.

The present disclosure relates to a cutting device suitable for penetrating and removing a strip from the material to be cut. The device is specifically intended to cut fiberglass, plaster, and any other material used for orthopedic casts, though it is not limited to these materials. It is further designed to be used in the removal of orthopedic casts from a patient.

FIG. 1 illustrates an orthopedic cast remover 101 equipped with a specially-designed cutting wheel assembly 102 and cutting shear 103. Cutting wheel assembly 102 is preferably equipped with two cutting wheels (see FIG. 2) that force a cast 105 or other material over a wide shear 103. The combination of the wheels and shear during operation separate a strip 104 of material from the plane of the cast 105. Under the exemplary embodiment, a cut strip is mechanically passed over the top surface of shear 103 and away from the cast surface. A channel (see dotted arrow, FIG. 2), also referred to as a passage, runs through the device allowing for the passage of the strip. The strip exits through the rear of the device.

Figure 2:
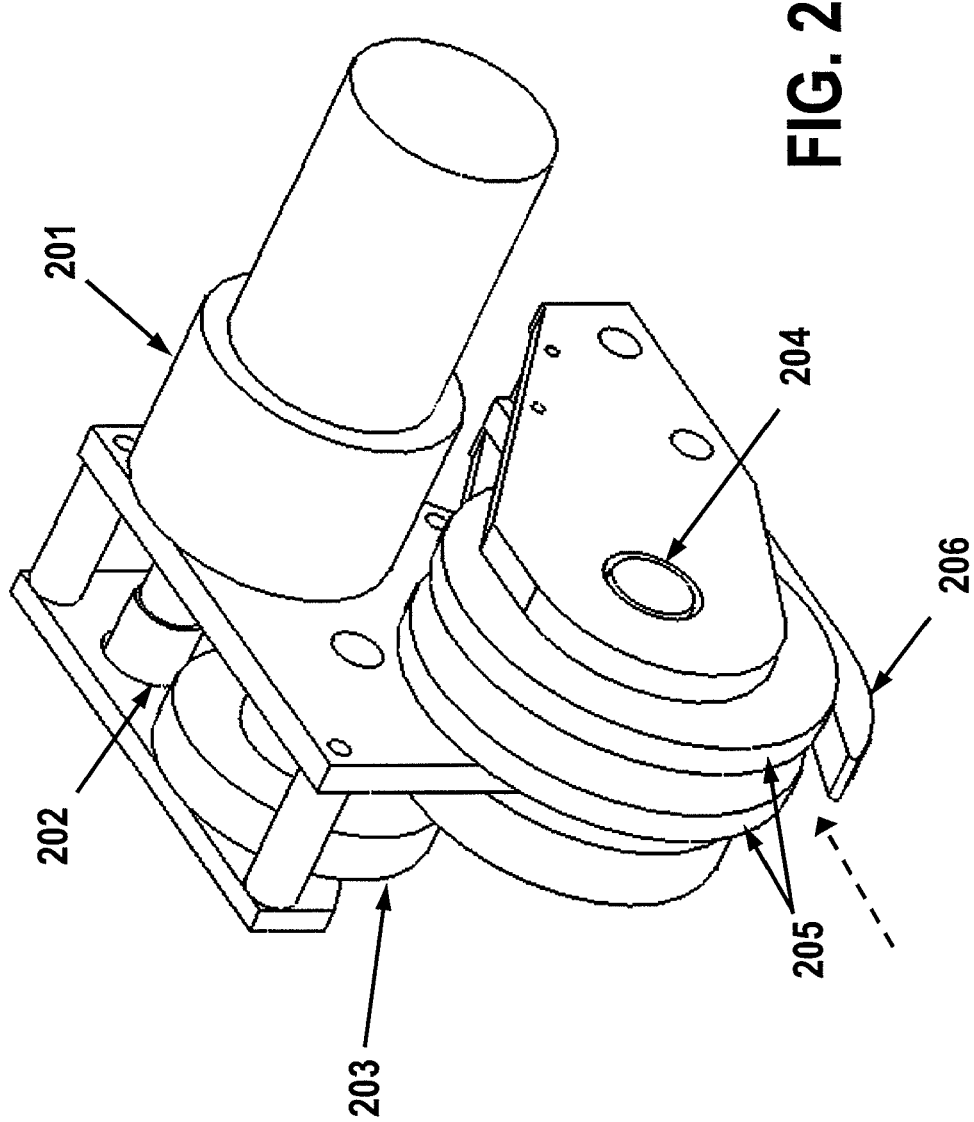
FIG. 2 is a side view of the orthopedic cast remover illustrated in FIG. 1.

A perspective view of the orthopedic cast remover of FIG. 1 is illustrated in FIG. 2. Under a preferred embodiment, the device is handheld, with mechanical power supplied by an electric motor 201. Power may be supplied through an appropriate power supply or an attached rechargeable battery. Under a preferred embodiment, the motor is a direct-current (DC) gear motor capable of producing continuous torque. One example of such a motor is a Pittman Lo-Cog® Gearmotor, model number GM9236S024, which may produce a continuous torque of 30 in-lbs and a no load speed of 71 RPM. Operation of the device is controlled through a switch. The switch should allow the motor to be powered for rotation in both directions. Alternatively, mechanical power may be supplied by hydraulic or pneumatic power.

Gear train 202 is configured to convert high-RPM, low torque output of electric motor 201 into a low-RPM, high torque output. Under the exemplary embodiment, a spur gear transmission (202, 203) is used to perform the necessary conversion. The transmission may be configured to provide a final gear ratio in the range between 20:1 and 25:1. This range of gear ratios would combine with the above referenced motor to result in a final RPM between 3.55 and 2.84, and a final torque between 600 and 750 in-lbs. It is understood by those skilled in the art that other configurations are available to achieve a low-RPM, high torque output, including, but not limited to worm gears, belts, pulleys or any other power transmission system. In an alternate embodiment, motor 201 may be separated from the cutting wheel assembly and power may be transferred using a flexible shaft. Gear transmission (202, 203) is configured to be coupled with a gear coupling affixed to a rotating shaft 204, which supplies rotational power to the wheels 205 of cutting wheel assembly, shown as an exploded view in FIG. 3. The cutting wheel assembly straddle a wide shear 206.

Figure 3:
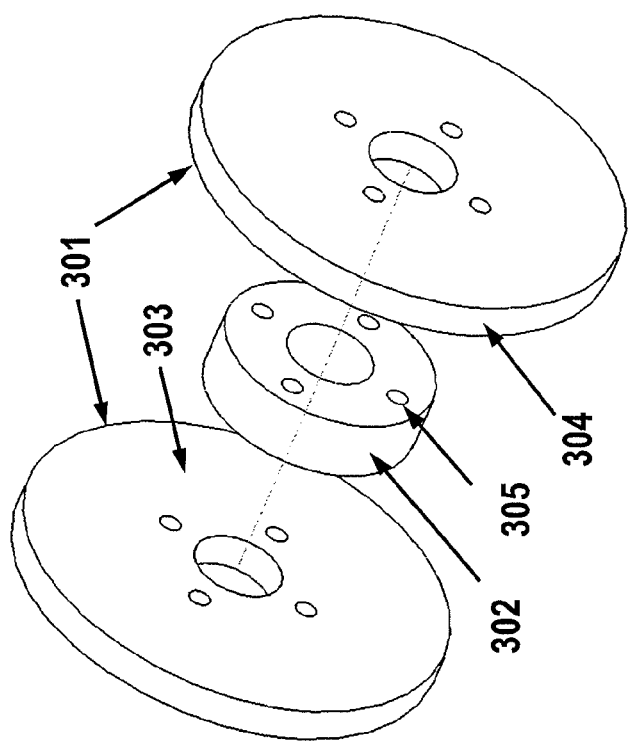
FIG. 3 illustrates an exploded view of a cutting wheel assembly for an orthopedic cast remover under the exemplary embodiments illustrated in FIGS. 1 and 2.

Under a preferred embodiment, cutting wheel assembly illustrated in FIG. 3 comprises two cutting wheels 301 and a hub 302. Each cutting wheel has a cutting surface 304 and an inner face (e.g., 303) that couples to a respective surface of hub 302. Hub 302 has tapped screw holes 305 that are used for attaching the cutting wheels as shown in FIG. 3. Under one exemplary embodiment, each cutting wheel has a diameter of approximately 3 inches, although any diameter may be used. A 3 inch diameter configured with the above referenced motor and gear ratio range will have a circumferential velocity between 0.56 and 0.45 inches per second. In general, the width of hub 302 determines the distance between the inner faces of the cutting wheels. Certain embodiments have a hub with a width equal to the width of a wide shear (405) to promote close contact between the inner faces of the wheels and the side surfaces of the shear.

Figure 4B:
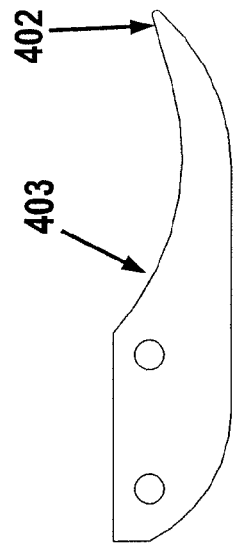
FIGS. 4A-4B illustrate a perspective view and side view of a wide shear for an orthopedic cast remover under the exemplary embodiments illustrated in FIGS. 1-3.
Figure 4A:
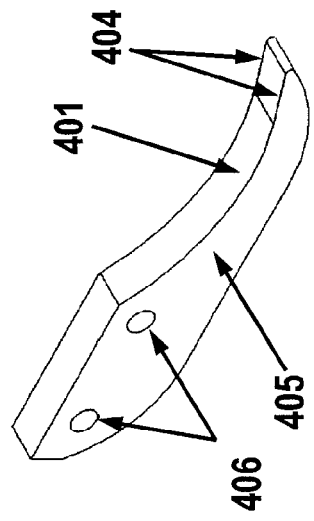

An exemplary wide shear is illustrated with various views in FIGS. 4A and 4B. Top surface 401 of shear preferably has a geometry that comprises straight 402 and curved 403 sections. Under this embodiment, edges 404 of the wide shear are at the intersection of the top and side surfaces 405 as illustrated in FIG. 4A. A position of the shear is maintained using supporting rods (not shown) that are inserted into mounting holes 406, where the supporting rods are held in place by the body 405. By mounting the shear through the sides as opposed to the top, the channel for passage of a strip during a cutting operation remains unobstructed.

Figure 5B:
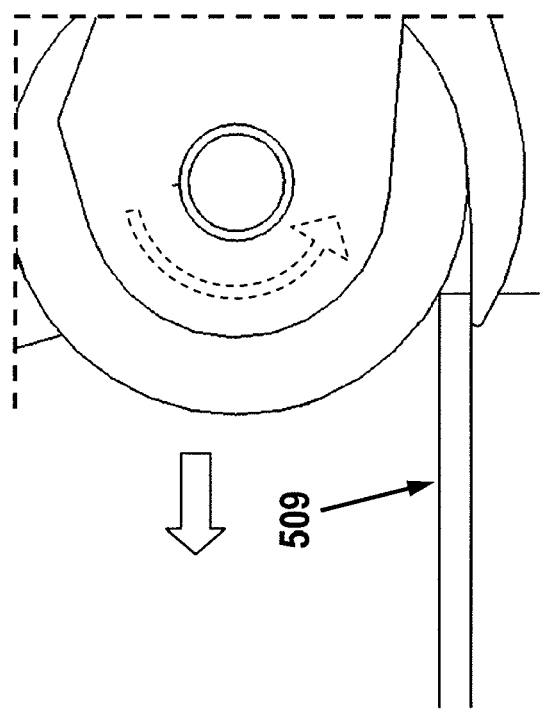
FIGS. 5A-5B illustrate a cutting wheel assembly and shear interface under an exemplary embodiment.
Figure 5A:
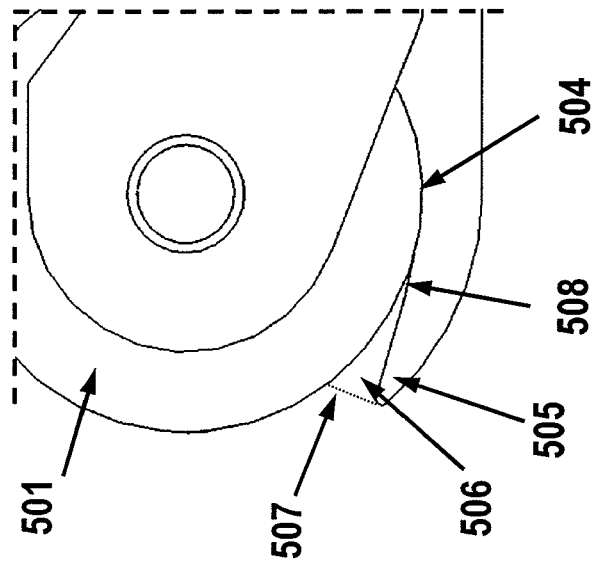

The geometry of the wheel and shear interface is illustrated in FIGS. 5A and 5B. When power is delivered to the device for forward/cutting operation, cutting wheels 501 spin in the direction indicated by the arrow in FIG. 5B so as to propel the device in the forward direction indicated by the block arrow in FIG. 5B when engaged with a surface 509, such as a cast. The bottom portion circumference of the cutting wheel 501 should overlap a certain distance with the top portion of the shear 504, but should not reach below the bottom of the shear. The inner face of overlapping portion of the cutting wheel is adjacent to the side surface of the wide shear. The tip of the shear 505 should protrude from the overlap of the cutting wheels (501).

This configuration produces a wedge shaped entry point 506 between the circumferential face of the wheels and the top of the shear. In profile, the wedge may be defined by the top of the shear, the circumference of the cutting wheel, and a line 507 perpendicular to the top of the shear intersecting with the circumference of the wheel. A portion of the material to be cut (509) is said to be "engaged" by the device when it lies within the wedge. Preferably, the material to be cut should be no thicker than opening of the wedge 506. The point of intersection of the circumference of the wheels with the corresponding edge of the wide shear is referred to as the pinch point 508. To begin cutting a surface 509, such as a cast, the device is placed at an end of the cast such that the tip of shear is beneath the cast, and the wheels are above the cast. Before cutting begins, the edge of the cast 509 is within the wedge of the device as seen in FIG. 5B. Once forward power is supplied to motor running and the wheels spinning, the device advances along the length of the cast.

FIGS. 6A-6C illustrate an exemplary engagement and cutting operation (fracturing) for a cutting wheel assembly and a shear. Shearing of the cast is accomplished through the interaction of the two circular cutting wheels 501 and the wide shear 504 situated between them. Wide shear 504 has two edges running along either side of the top of the shear, where each edge interacts with one of the cutting wheels. The fracturing process begins in FIG. 6A. As an engaged portion of the material to be cut 601 proceeds towards the pinch point, the distance between the cutting wheel circumference 603 and the top of the shear 604 lessens. When this distance becomes less than the thickness of the material, a stress is exerted upon the material, resulting in deformation 605, shown in FIG. 6B. As the distance continues to decrease, the stress will surpass the ultimate tensile strength of the material, and fracturing 606 will occur, shown in FIG. 6C. Due to the thickness and brittle nature of cast shell materials, fracturing will occur at a point prior to the pinch point.

Typical fracturing under the exemplary embodiment occurs on both sides of the shear at the same time. The wheels move continuously. As such, the fracturing is a constant process and renders the cast as depicted in FIG. 7. The process results in a fractured trough 703 and a continuous strip of the severed cast 701. The fracturing process continues along remainder 702. Over the course of cast removal, the remainder is stationary, leaving it consistent in its position relative to the portion of the body of the patient to which it corresponds. The strip (701) is forced above the outer surface of the remainder (702). In this way it can be thought that the wide shear lifts the portion of the cast that will become the strip past the cutting wheels.

Figure 8:
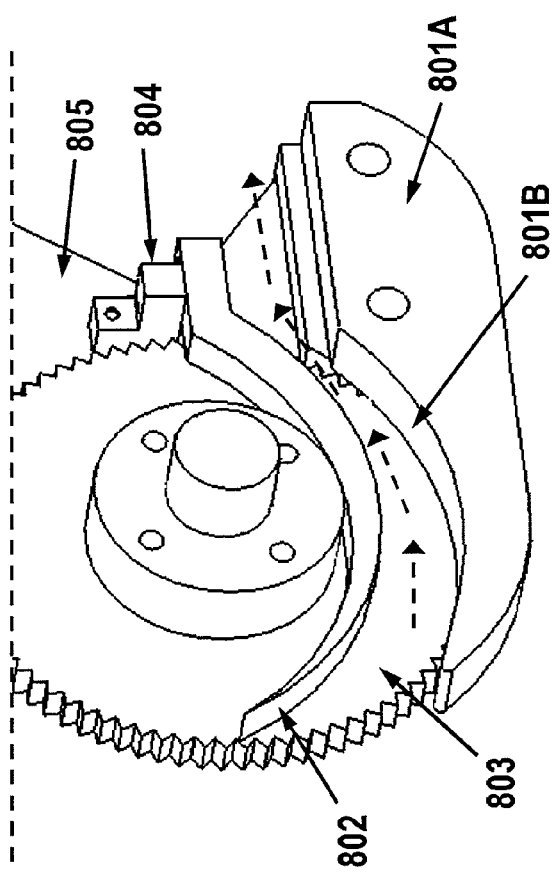
FIG. 8 illustrates an orthopedic cast remover having a deflector assembly under another exemplary embodiment.

Turning to FIG. 8, a body 805 of the exemplary embodiment supports shear 801A by the sides of the shear so that the space above the shear remains unobstructed. This allows for an open channel to run from the front to the back of the device as shown in FIG. 8. The channel's contours are defined by the top of the shear 801B, the inner faces of the cutting wheels (one shown) 803 and the bottom surface of the deflector 802. During operation, a severed strip of material would run through the channel and out the back of the device, shown as dotted arrows in FIG. 8. The deflector 802 serves to prevent the strip from getting caught between the inner faces of the cutting wheels. Under a preferred embodiment, deflector 802 is attached to a deflector mount 404, which is itself attached to the body 805.

The dual-fracturing process described above is distinguishable from conventional processes in a number of ways. When fracturing a thick, brittle material, the cutting surface does not require a sharp edge, since the disclosed embodiments rely on opposing forces to break the material rather than on the puncture and cleaving action associated with a shear. Accordingly, certain embodiments disclosed herein accomplish the fracturing of a shell of a cast using a bladeless design. Another distinguishable difference relates to the position of the cut material after it has been sheared. With a typical single shear, the material is cut into two portions separated by a slit. No material is removed. Both portions remain in the plane in which they were cut. The shear then travels between the two portions. The width of the slit is determined by the width of the shearing components.

In contrast, the embodiments of the present disclosure cut the material into three portions. The middle portion—referred to as the strip—is angled out of the plane of cutting as it traverses the top surface of the shear. The result is that the shearing mechanism is not in between the portions, but the cutting wheels are above their corresponding portions of the material, and the wide shear is below its corresponding portion. The resulting position of the cut material is particularly relevant when cutting a thick, rigid material such as an orthopedic cast. Single shears generally rely on the lack of rigidity to permit their passage through the slit. With a rigid material, restorative forces of the material exert a force normal to the external faces of the shear, making advancement of the shear through the material difficult. The presently disclosed embodiments avoid such difficulties. During shearing, a shear travels through a trough (703) created by the fracturing method, and the strip travels through the channel.

Certain embodiments may incorporate a shear with enhancements to the top surface 401 or edges 404. These enhancements may be located anywhere along the length of the surface or edge of the shear as is disclosed in greater detail in connection with FIGS. 11A-11C below.

Figure 9:
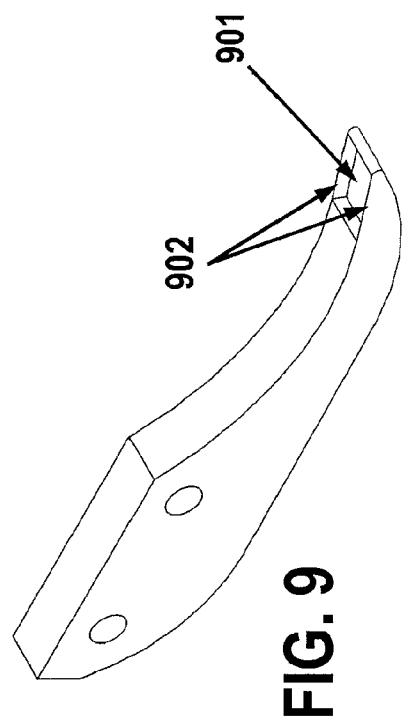
FIG. 9 illustrates a shear having a recessed area under another exemplary embodiment.

Turning to FIG. 9, the top surface of a shear may be configured with a recessed area 901 at any point along its length. The recessed area 901 is advantageously suited to aid in the flow of the strip during fracturing. Recessed area 901 may be designed such that it isolates the edges from the rest of the surface. Also among the possible enhancements to the shear is a sharpened edge. When placed along the portion of the shear where shearing occurs 902, a sharp edge may help to cut the padding layer of the cast.

Figure 10A:
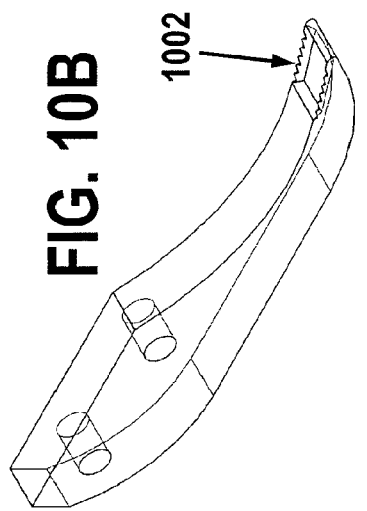
FIGS. 10A-10B illustrate shears having recessed areas as described in FIG. 9, and further having textured surfaces with scalloped and/or serrated edges under another exemplary embodiment.
Figure 10B:
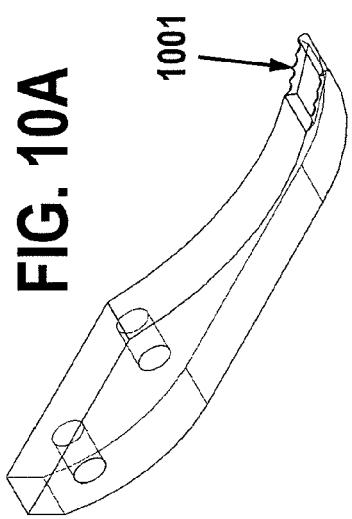

Further enhancements are illustrated in FIGS. 10-10B, where the sharpened edges may be configured with a scalloped edge 1001. When placed along the portion of the shear where shearing occurs, a scalloped edge would help to cut the padding layer of the cast. A scalloped edge may also score the inside of the cast shell thereby reducing the required force of fracturing the cast. Additionally, the sharpened edge may be configured with a serrated edge 1002. When placed along the portion of the shear where shearing occurs, a serrated edge may help to cut the padding layer of the cast. A serrated edge may also score the inside of the cast shell thereby reducing the required force of fracturing the cast. It is understood by those skilled in the art that other types of edges, such as saw tooth or diamond edges, or even combinations of edges, are contemplated in the present disclosure.

Figure 11A:
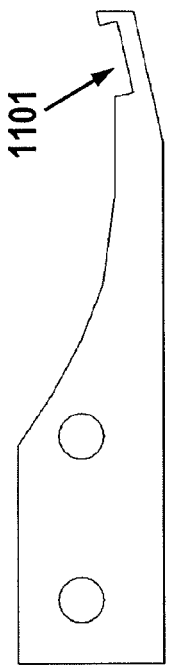
FIGS. 11A-11C illustrate various shear bases equipped with shear insert areas along a shearing arm.
Figure 11B:
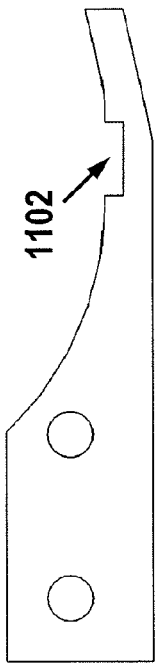
Figure 11C:
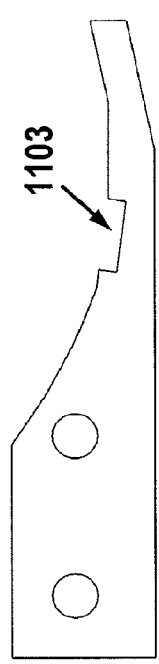
Figure 12:
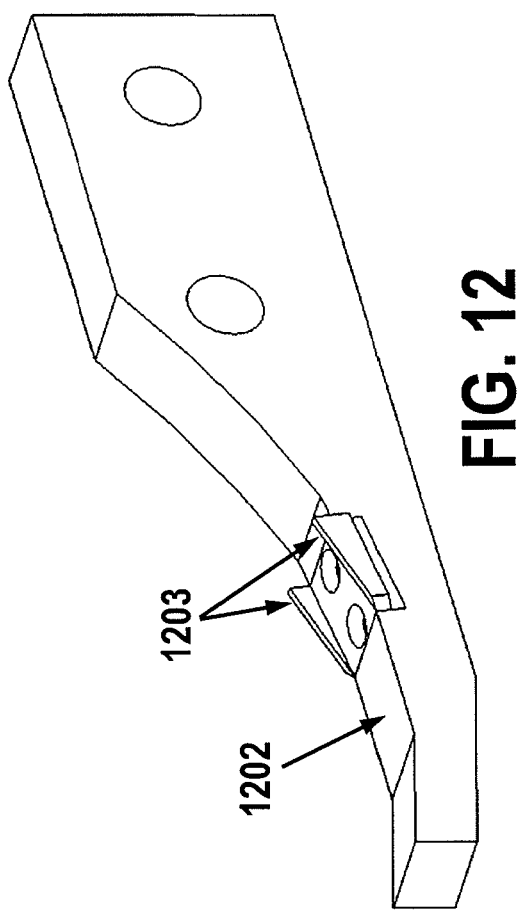
FIG. 12 illustrates an exemplary shear base equipped with an insert as described above in FIGS. 11A-11C.

In addition to recessed areas and edges, certain embodiments may be configured with shear enhancements through use of inserts, illustrated in FIGS. 11A-11C. In such a configuration, openings may be made anywhere along the surface of the shear base (1101-1103) to accommodate any suitable insert. The use of inserts would provide several advantages: the insert may be replaceable, it may be made of a special material which would be too expensive for the entire shear, or it may have a shape which would be difficult to incorporate into the design and manufacturing of the shear-base, as illustrated in FIG. 12. Here, an insert having elevated edges 1203 is configured in a rear portion of shear base 1202 to provide advantageous cutting and guidance for material being fractured.

Figure 13:
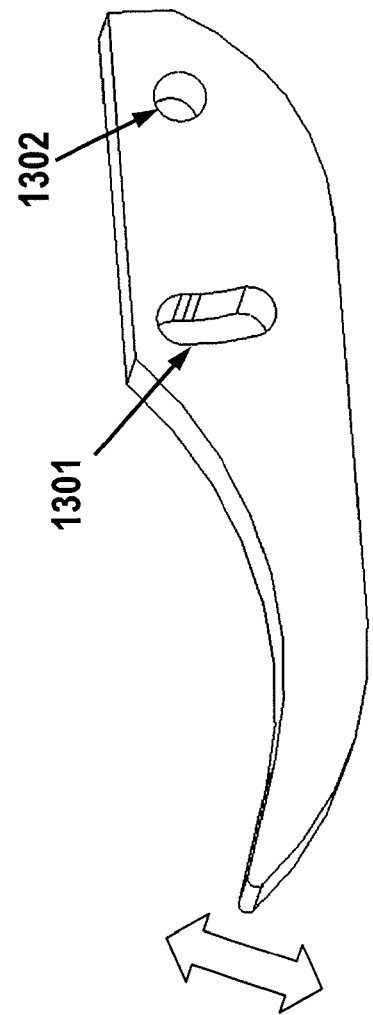
FIG. 13 illustrates a shear equipped with an arced slot to allow adjustment under an exemplary embodiment.

In addition to inserts, the shear of certain embodiments may be modified so that its angle relative to the body may be adjusted. The modified shear and adjustability are depicted in FIG. 13. In this embodiment, the forward mounting hole has been modified to be an arced slot 1301, where the center of the arc is the rear mounting hole 1302. Rotating the shear about the rear hole allows for adjustability indicated by the block arrow shown in FIG. 13.

In certain embodiments, one or more cutting wheels may incorporate enhancements to the circumferential face to provide additional benefits. Turning to FIG. 14A, an exemplary cutting wheel is configured with an arrangement of teeth (1401) along the circumference. The teeth 1401 are illustrated as having a generally triangular shape resembling gear teeth. The teeth can be of any pitch. It is understood that any of a variety of shapes and patterns may be employed.

Figure 14B:
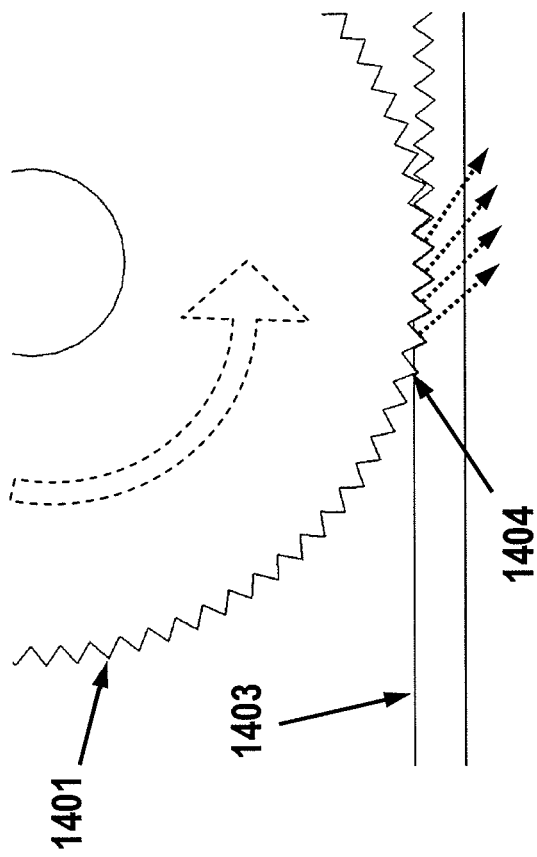
FIGS. 14A-14B illustrate an exemplary arrangement of teeth on one or more cutting wheels of a cutting wheel assembly, and the effect of the arrangement on a cutting surface under an exemplary embodiment.
Figure 14A:
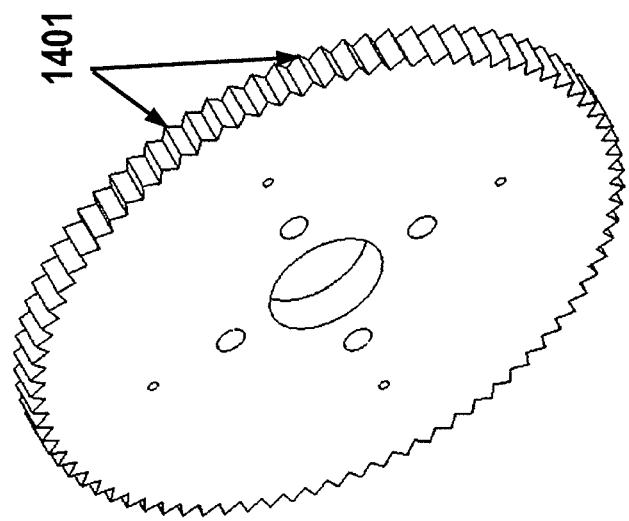

Under the gear teeth embodiment, the effects of teeth on the wheel are depicted in FIG. 14B, and are described as follows. In use, the teeth 1401 on a rotating cutting wheel descend upon the surface of the material 1403 as it approaches a pinch point (depicted as dotted block arrow in FIG. 14B). The point of pressure of the tooth 1404 will eventually puncture the surface of the material. As each tooth sinks into surface 1403, traction forces (illustrated by dotted arrows in FIG. 14B) will be applied to the surface relative to the cutting wheel(s) as it pushes the material past the fracture point. The punctures will also serve as perforations in the material, lessening the requisite force of fracture at the locations of the puncture.

Some materials, notably plaster, have the tendency to crumble when punctured by a tooth. The result of successive tooth punctures in plaster is to wear away the surface of the plaster to the depth of the tooth, resulting in no additional traction for the cutting wheel. To counter this occurrence, an embodiment of the present invention may incorporate a cutting wheel with spaced teeth as depicted in FIGS. 15A-15B. In the exemplary embodiment of FIG. 15A, the cutting wheel has a "1-on-5-off" pattern while the cutting wheel in FIG. 15B has a "1-on-3-off" pattern. Where teeth are removed on cutting wheel 15A, the edge of the wheel is straight 1501, while on cutting wheel 15B the edges are curved 1502. Such patterns permit sufficient material between successive tooth puncturing such that the plaster may retain its structural integrity, and the teeth may supply traction to the cutting wheel.

Similar effects of gear teeth may be achieved through knurling the circumferential face of the cutting wheels. Knurled teeth could have a straight, spiral, criss-cross, concave or convex patterned teeth of any pitch. Similarly to variations with gear teeth, the knurled surface may have patterns which are preferential for use on certain materials.

Under yet another exemplary embodiment illustrated in FIG. 16, cutting wheel 1602 is configured to incorporate an internal blade 1602 (also referred to as an inner blade). Under a preferred embodiment, inner blade 1601 is sandwiched between the cutting wheel 1602 and hub 1603. The inner blade 1602 is operative to cut any padding accompanying a cast. It is concentric with the external cutting wheel 1602.

Figure 17:
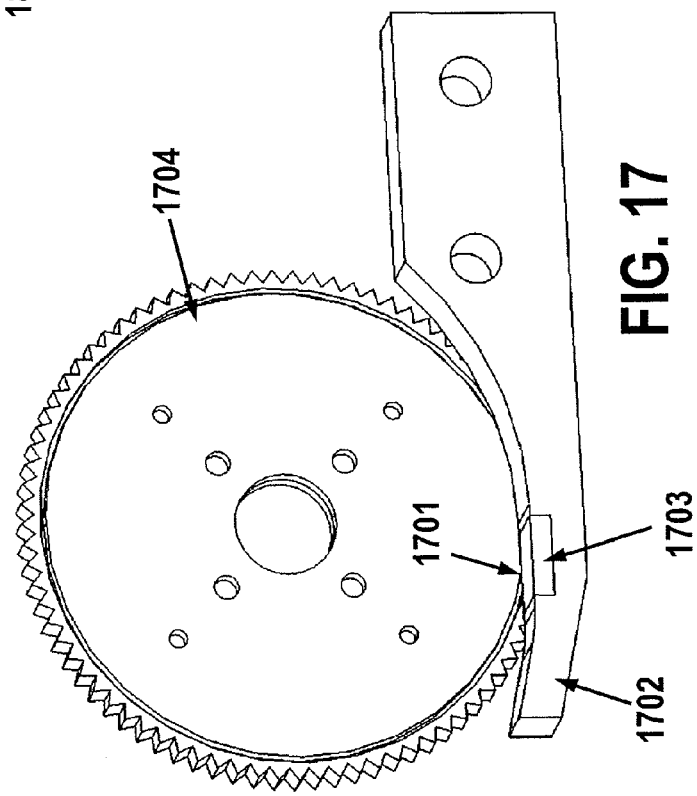
FIG. 17 illustrates an exemplary interaction of an inner blade with a shear.

FIG. 17 illustrates an exemplary interaction of inner blade 1704 with shear 1702. The pinch point 1701 of the internal cutting wheel with the shear 1702 is posterior to the pinch point for the external cutting wheel and shear 1702. The edge of the inner blade 1704 may further interact with a shear-insert 1703 as depicted in FIG. 17, or with the edge of the shear.

Figure 18A:
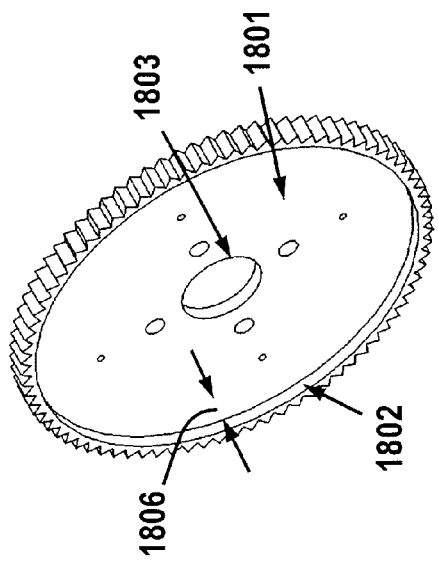
FIGS. 18A-18B illustrate a modified cutting wheel that incorporates an inner blade under an exemplary embodiment.
Figure 18B:
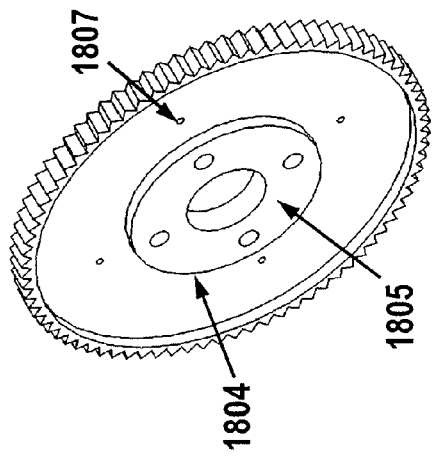

FIGS. 18A and 18B illustrate cutting wheels modified to incorporate an internal cutting wheel. The internal wheel should be configured to sit in a recessed portion 1801 of the cutting wheel. The depth of the recess may be equal to or greater than the thickness of the internal cutting wheel. The diameter of the recess should be larger than the internal cutting wheel, such that a void 1806 exists between the wall of the recess of the external cutting wheel 1802 and the edge of the internal cutting wheel (1601). The recess in the external cutting wheel may begin at a bore 1803 and proceed radially outward as shown in FIG. 18A, or may begin at a radius greater than the bore 1804 resulting in an annulus 1805 of non-recessed material around the bore as illustrated in FIG. 18B. The internal cutting wheel will correspond to the shape of the recess, having either a bore equal to the bore of the external cutting wheel, or a bore equal to the outer diameter of the annulus. Under a preferred embodiment, the internal cutting wheel(s) mounts to the external cutting wheel(s) using a plurality screw holes 1807, and the cutting wheel assembly is attached to a hub. If the cutting wheel assembly uses the annulus design (FIG, 18B), the annulus is in contact with the hub; otherwise the internal cutting wheel contacts the hub.

Figure 19A:
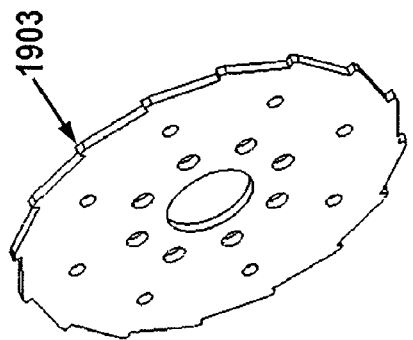
FIGS. 19A-19C illustrate a plurality cutting wheel configurations utilizing different cutting geometries.
Figure 19B:
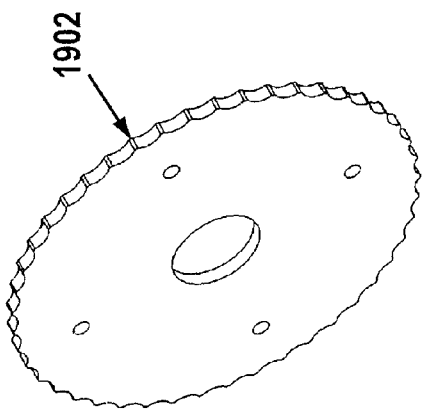
Figure 19C:
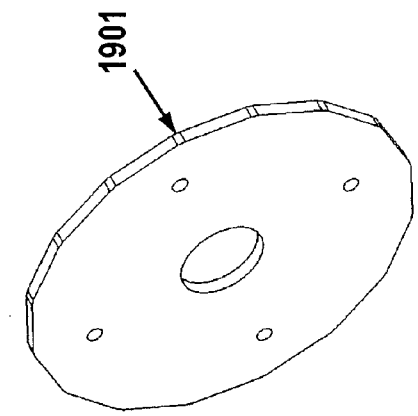

FIGS. 19A-19C illustrate other exemplary embodiments directed to inner blades having edges contoured to aid in cutting material such as cast padding. In the embodiment of FIG. 19A, the edge is contoured to have flat faces 1901. During operation, these faces would create an action more resembling shearing as compared to a perfectly round inner blade. In FIG. 19B, the inner blade may incorporate an edge contoured to have a scalloped edge 1902. In FIG. 19B, the inner blade may incorporate an edge contoured to have a serrated design 1903. It is understood by those skilled in the art that other contoured edges are contemplated in the present disclosure.

Figure 20:
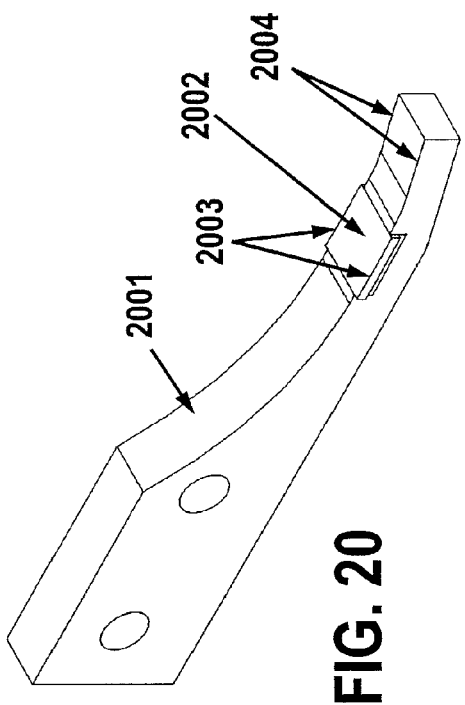
FIG. 20 illustrates a shear adapted with an insert to interact with an inner blade of a cutting wheel assembly under another exemplary embodiment.

Certain embodiments of an inner blade cutting wheel assembly may have a recess 1801 greater than the thickness of an inner blade. For such embodiments, given that an edge of the cutting wheel interacts with the edge of the shear, a portion of the shear or an insert on the shear must be wider than the distance between the cutting wheel edges in order to interface with the inner blades. Turning to FIG. 20, a shear 2001 is disclosed having an insert 2002 adapted for such a configuration. Here, the edges 2003 of insert 2002 are configured to interact with the inner blade edges and are removed from the edges 2004 of the shear-base.

Figure 21:
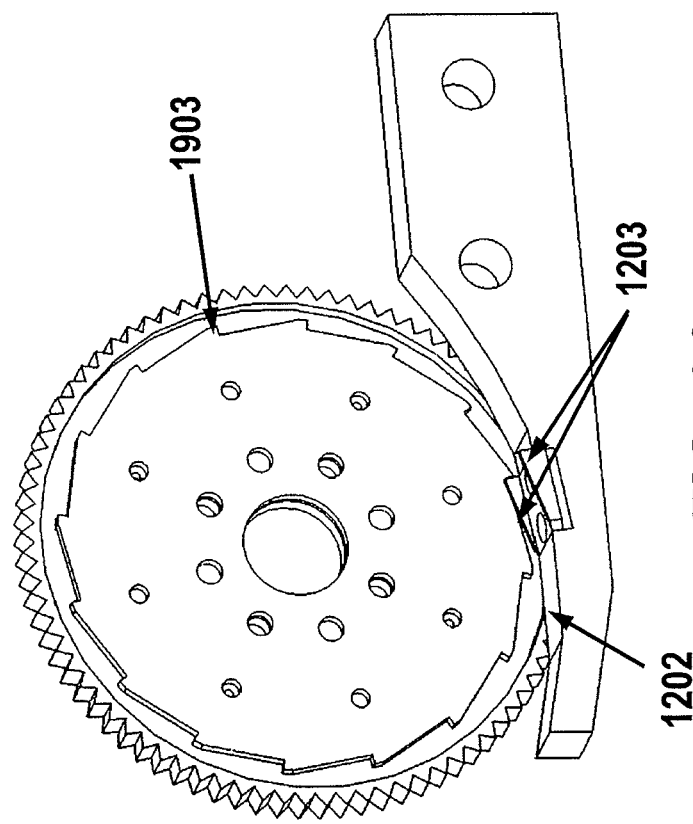
FIG. 21 illustrates an alternate embodiment where an insert interacts with an inner blade of a cutting wheel assembly

Turning to FIG. 21, an embodiment is disclosed utilizing a shear-base with inserts (e.g., see FIG. 12) together with an inner blade configured with contoured edges (e.g., see FIG. 19C). The insert has edges 1203 angled relative to the top surface 1202 of the portion of the shear upon within which it rests. Under this configuration, the angled edges 1203 interact in a nearly coincident fashion with the passing edges of the serrated blade 1903, much like a pair of scissors. During operation, the angled edges 1203 lift the material being cut, such as padding, to assist in the cutting process. This also adds tension to the padding making it easier to cut. The raised edges also allow for more flexibility regarding the contours of the serrated inner blade.

Figure 22:
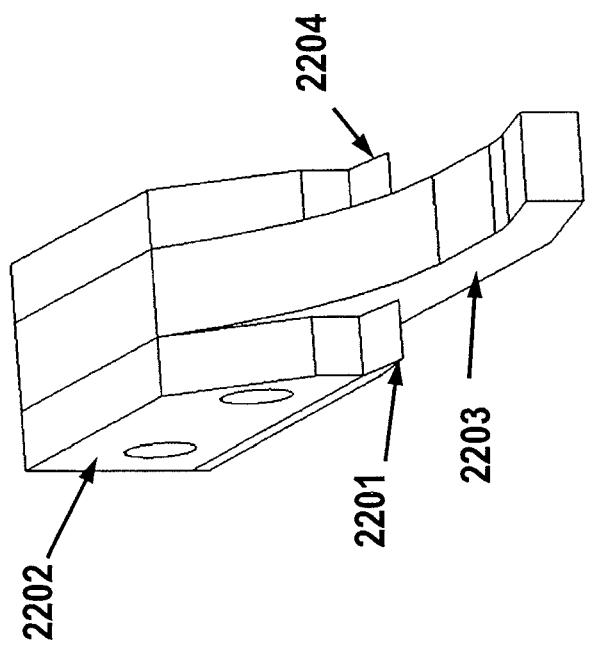
FIG. 22 illustrates yet another exemplary embodiment utilizing secondary bales to complement a shear for a cutting wheel assembly.

Other embodiments of the current design may incorporate stationary secondary blades for the purposes of cutting additional material, such as padding. One such embodiment is illustrated in FIG. 22. Here, secondary blades (2201, 2204) are mounted to a portion of the body 2202 located at the sides of the shear 2203. The sharp edge of the blades (2201, 2204) preferably point towards the forward direction of the device. Thus, the blades are placed so as to engage the material (intact padding) as it is pulled taught by the increasing distance between the corresponding strip and remainder of the cast.

Figure 23:
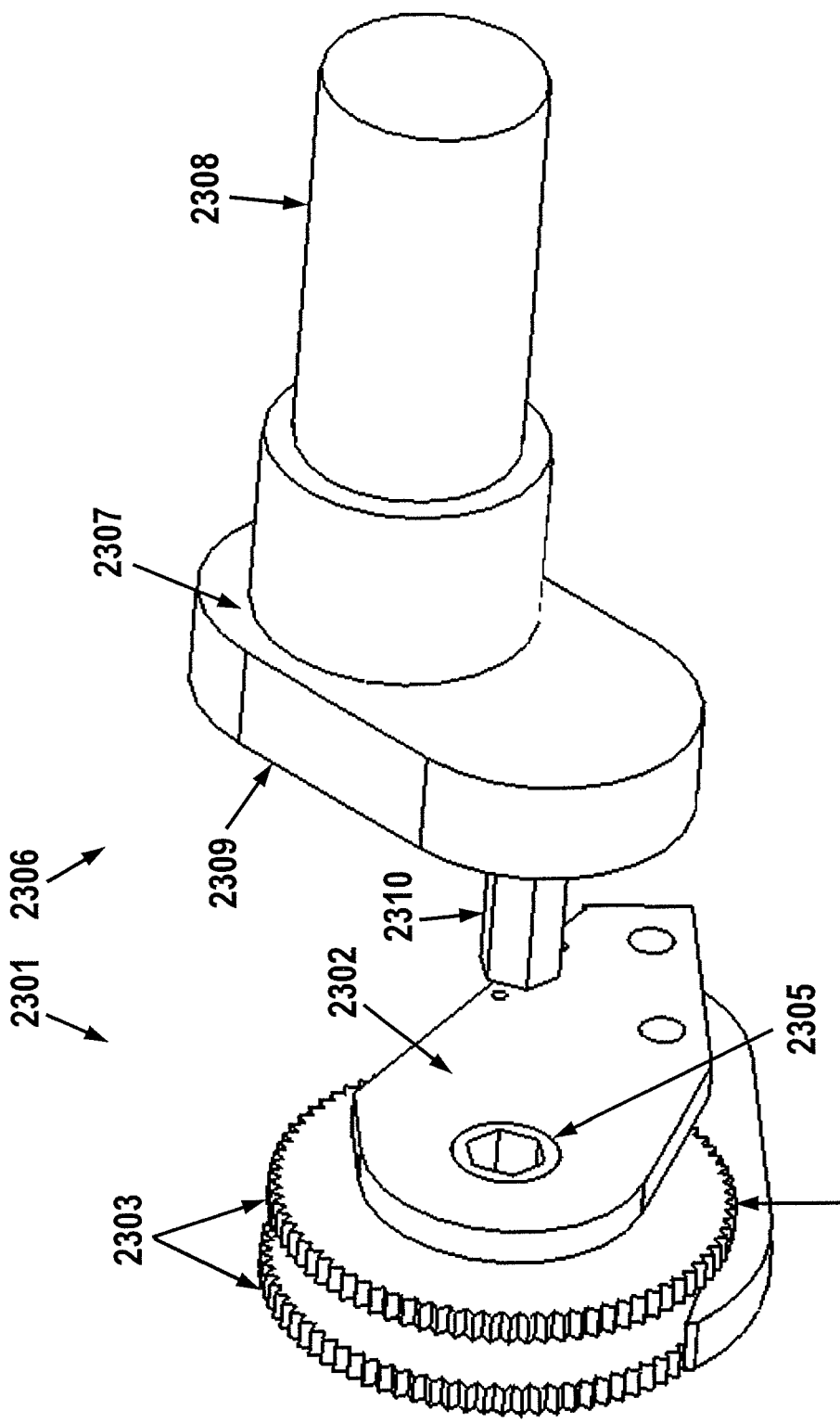
FIG. 23 illustrates a cutting wheel assembly utilized together with a drive assembly under yet another exemplary embodiment.

The cutting/shear assembly may be configured in a manner to make it detachable from a drive assembly. One exemplary configuration is illustrated in FIG. 23, where the cutting assembly 2301 includes a body 2302, a cutting wheel assembly 2303, a shear 2304, and a modified shaft coupling 2305. The drive assembly 2306 includes a body 2307, a motor 2308, and the drive train 2309 with a modified output shaft 2310. In the embodiment of FIG. 23 the output shaft 2310 is hexagonal and the shear assembly shaft coupling 2305 has a hexagonal bore, but any acceptable method of transferring the rotational power is acceptable.

The detachable shear assembly illustrated in FIG. 23 has several advantages. The detachable shear assembly will allow for replacing shear assemblies that have reached the end of their useful life. Different shear assemblies may have advantages for removing casts of different shapes and constructions. A detachable shear assembly will allow the device operator to choose from a selection of shear assemblies based on the cast removal at hand. Aspects to consider when selecting an appropriate shear assembly could include cast material (plaster, fiberglass, combination), cast thickness, radius of curvature of cast, etc. Different shear assemblies consist of different combinations of aforementioned shear and cutting wheel assemblies.

Although various embodiments of the present invention have been described with reference to a particular arrangement of parts, features and the like, these are not intended to exhaust all possible arrangements or features, and indeed many other embodiments, modifications and variations will be ascertainable to those of skill in the art. For example, while embodiments were disclosed relating to media data and content, other embodiments are envisioned where panelist purchase data, panelist metadata, and other forms of data capable of having an individualized identification are processed in the aforementioned network.

The Abstract of the Disclosure is provided to comply with 37 C.F.R. .sctn.1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. An apparatus for removing a strip of a rigid orthopedic material, the apparatus comprising:

a cutting wheel assembly comprising a hub, a first cutting wheel and a second cutting wheel, the hub having a smaller diameter than a diameter of the first cutting wheel and a diameter of the second cutting wheel, wherein the hub is coupled between the cutting wheels to form a passage between an inner face of the first cutting wheel and an inner face of the second cutting wheel; and a shear coupled to the cutting wheel assembly and positioned below the passage, the shear comprising a top surface having a first edge configured to be engaged with the inner face of the first cutting wheel, and a second edge configured to be engaged with the inner face of the second cutting wheel;

wherein at a point tangential to the rigid orthopedic material, the first and second cutting wheels rotate in a direction opposite to the removal direction to cause the cutting wheel assembly and the shear to exert opposing forces on the rigid orthopedic material;

wherein the shear is configured to allow the material to pass over the top surface and be fractured by the cutting wheel assembly into a predetermined width defined by the first and second edge; and further comprising a deflector positioned within the passage and above the shear.

2. An apparatus for removing a strip of rigid orthopedic material in a removal direction from a first location to a second location of the orthopedic material, the apparatus comprising:

a cutting wheel assembly comprising a hub, a first cutting wheel and a second cutting wheel, the hub having a smaller diameter than a diameter of the first cutting wheel and a diameter of the second cutting wheel, wherein the hub is coupled between the cutting wheels to form a passage between an inner face of the first cutting wheel and an inner face of the second cutting wheel; and a shear coupled to the cutting wheel assembly and positioned below the passage, the shear comprising a top surface having a first edge configured to be engaged with the inner face of the first cutting wheel, and a second edge configured to be engaged with the inner face of the second cutting wheel;

wherein at a point tangential to the rigid orthopedic material, the first and second cutting wheels rotate in a direction opposite to the removal direction to cause the cutting wheel assembly and the shear to exert opposing forces on the rigid orthopedic material;

wherein the shear is configured to allow the material to pass over the top surface and be fractured by the cutting wheel assembly into a predetermined width defined by the first and second edge; and wherein the shear comprises a plurality of sharp edges in an area of the top surface.

3. The apparatus according to claim 2, wherein the sharp edges have one of a scalloped and serrated pattern.

4. The apparatus according to claim 3, wherein the shear comprises an opening on the top surface, the opening configured to accept an insert for assisting in removing the fractured material.

5. The apparatus according co claim 4, wherein the insert comprises a device comprising elevated edges.

6. An apparatus for removing a strip of rigid orthopedic material in a removal direction from a first location to a second location of the orthopedic material, the apparatus comprising:

a cutting wheel assembly comprising a hub, a first cutting wheel and a second cutting wheel, the hub having a smaller diameter than a diameter f the first cutting wheel and diameter of the second cutting wheel, wherein the hub is coupled between the cutting wheels to form a passage between an inner face of the first cutting wheel and an inner face of the second cutting wheel; and a shear coupled to the cutting wheel assembly and positioned below the passage, the shear comprising a top surface having a first edge configured to be engaged with the inner face of the first cutting wheel, and a second edge configured to be engaged with the inner face of the second cutting wheel;

wherein at a point tangential to the rigid orthopedic material, the first and second cutting wheels rotate in a direction opposite to the removal direction to cause the cutting wheel assembly and the shear to exert opposing forces on the rigid orthopedic material; and wherein the shear is configured to allow the material to pass over the top surface and be fractured by the cutting wheel assembly into a predetermined width of the strip defined by the first and second edge, further comprising a first and second inner cutting wheel, wherein the first inner cutting wheel is positioned between the inner face of the first cutting wheel and the hub, and the second inner cutting wheel is positioned between the inner face of the second cutting wheel and the hub.

7. The apparatus according to claim 6, wherein diameters of the first inner cutting wheel and second inner cutting wheel is smaller than diameters of the first cutting wheel and the second cutting wheel.

8. The apparatus according to claim 7, wherein the diameters of the first inner cutting wheel and second inner cutting wheel is greater than the diameter of the hub.

9. An apparatus for removing a strip of rigid orthopedic material in a removal direction from a first location to a second location of the orthopedic material, the apparatus comprising:

a cutting wheel assembly comprising a hub, a first cutting wheel and a second cutting wheel, the hub having a smaller diameter than a diameter of the first cutting wheel and a diameter of the second cutting wheel, wherein the hub is coupled between the cutting wheels to form a passage between an inner face of the first cutting wheel and an inner face of the second cutting wheel; and a shear coupled to the cutting wheel assembly and positioned below the passage, the shear comprising a top surface having a first edge configured to be engaged with the inner face of the first cutting wheel, and a second edge configured to be engaged with the inner face of the second cutting wheel;

wherein at a point tangential to the rigid orthopedic material, the first and second cutting wheels rotate in a direction opposite to the removal direction to cause the cutting wheel assembly and the shear to exert opposing forces on the rigid orthopedic material; and wherein the shear is configured to allow the material to pass over the top surface and be fractured by the cutting wheel assembly into a predetermined width defined by the first and second edge, wherein the shear comprises a first stationary blade and a second stationary blade, the first stationary blade positioned on one side of the shear and the second stationary blade positioned on another side of the shear.

10. The apparatus according to claim 9, wherein the first and second stationary blades are positioned in an area that is at least partly outside the passage.

11. The apparatus according to claim 9, wherein the first and second stationary blades are positioned to be behind a front portion of the shear.

* * * * *